(12) United States Patent
Finke et al.

(10) Patent No.: US 9,341,575 B2
(45) Date of Patent: May 17, 2016

(54) USE OF SIGNAL ENHANCING COMPOUNDS IN ELECTROCHEMILUMINESCENCE DETECTION

(71) Applicant: Roche Diagnostics Operations, Inc., Inadianapolis, IN (US)

(72) Inventors: Andreas Finke, Penzberg (DE); Bernhard Hauptmann, Penzberg (DE); Johannes Stoeckel, Munich (DE); Michaela Windfuhr, Iffeldorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 36 days.

(21) Appl. No.: 13/844,778

(22) Filed: Mar. 15, 2013

(65) Prior Publication Data

US 2013/0224758 A1 Aug. 29, 2013

Related U.S. Application Data

(63) Continuation of application No. PCT/EP2011/068540, filed on Oct. 24, 2011.

(30) Foreign Application Priority Data

Oct. 25, 2010 (EP) .................................... 10188716
Nov. 22, 2010 (EP) .................................... 10192106

(51) Int. Cl.
*B01L 3/00* (2006.01)
*G01N 21/66* (2006.01)
*G01N 21/76* (2006.01)

(52) U.S. Cl.
CPC .......... *G01N 21/76* (2013.01); *B01L 3/502715* (2013.01); *B01L 3/502761* (2013.01); *G01N 21/66* (2013.01)

(58) Field of Classification Search
None
See application file for complete search history.

(56) References Cited

U.S. PATENT DOCUMENTS

| 4,002,456 A | 1/1977 | Maas |
| 4,554,088 A | 11/1985 | Whitehead et al. |
| 4,628,037 A | 12/1986 | Chagnon et al. |
| 4,695,393 A | 9/1987 | Chagnon et al. |
| 4,698,302 A | 10/1987 | Whitehead et al. |

(Continued)

FOREIGN PATENT DOCUMENTS

| CN | 101246125 A | 8/2008 |
| EP | 0441875 B1 | 8/1991 |

(Continued)

OTHER PUBLICATIONS

International Search Report issued Jan. 18, 2012 in Application No. PCT/EP2011/0608540, 4 pages.

(Continued)

*Primary Examiner* — Mark Shibuya
*Assistant Examiner* — Gary E Hollinden
(74) *Attorney, Agent, or Firm* — Stinson Leonard Street LLP

(57) ABSTRACT

The application provides methods for the detection of an analyte in a sample by electrochemiluminescence using certain reagent compositions. Reagent compositions, reagent kits for measuring electrochemiluminescence (ECL) and electrochemiluminescence detection methods using the reagent compositions are disclosed. In particular, the application relates to the use of novel combinations of compounds, which can be used in said measurements to provide improved ECL assay performance.

16 Claims, 3 Drawing Sheets

(56) References Cited

U.S. PATENT DOCUMENTS

| | | | |
|---|---|---|---|
| 4,965,392 A | 10/1990 | Fritzberg et al. | |
| 5,093,268 A | 3/1992 | Leventis et al. | |
| 5,147,806 A | 9/1992 | Kramin et al. | |
| 5,202,238 A | 4/1993 | Fell, Jr. et al. | |
| 5,204,244 A | 4/1993 | Fell et al. | |
| 5,240,863 A | 8/1993 | Shibue et al. | |
| 5,308,754 A | 5/1994 | Kankare et al. | |
| 5,310,687 A | 5/1994 | Bard et al. | |
| 5,324,457 A | 6/1994 | Zhang et al. | |
| 5,543,112 A | 8/1996 | Ghead et al. | |
| 5,591,581 A | 1/1997 | Massey et al. | |
| 5,597,910 A | 1/1997 | Gudibande et al. | |
| 5,641,623 A | 6/1997 | Martin | |
| 5,643,713 A | 7/1997 | Liang et al. | |
| 5,677,192 A | 10/1997 | Klemt et al. | |
| 5,679,519 A | 10/1997 | Oprandy | |
| 5,705,402 A | 1/1998 | Leland et al. | |
| 5,723,342 A * | 3/1998 | Giesen et al. | 436/172 |
| 5,731,147 A | 3/1998 | Bard et al. | |
| 5,779,976 A * | 7/1998 | Leland et al. | 422/52 |
| 5,786,141 A | 7/1998 | Bard et al. | |
| 5,846,485 A | 12/1998 | Leland et al. | |
| 5,866,434 A | 2/1999 | Massey et al. | |
| 5,935,779 A | 8/1999 | Massey et al. | |
| 6,066,448 A | 5/2000 | Wohlstadter et al. | |
| 6,099,760 A | 8/2000 | Jameison et al. | |
| 6,136,268 A | 10/2000 | Ala-Kleme et al. | |
| 6,140,045 A | 10/2000 | Wohlstadter et al. | |
| 6,207,369 B1 | 3/2001 | Wohlstadter et al. | |
| 6,251,690 B1 * | 6/2001 | Kulmala et al. | 436/518 |
| 6,316,607 B1 | 11/2001 | Massey et al. | |
| 6,919,173 B2 | 7/2005 | Tsionsky et al. | |
| 6,994,971 B1 * | 2/2006 | Straume et al. | 435/6.16 |
| 8,852,922 B2 * | 10/2014 | Glezer et al. | 435/288.5 |
| 2001/0018187 A1 | 8/2001 | Sun et al. | |
| 2003/0124572 A1 | 7/2003 | Umek et al. | |
| 2007/0116600 A1 | 5/2007 | Kochar et al. | |
| 2009/0178924 A1 * | 7/2009 | Ala-Kleme et al. | 204/403.06 |
| 2013/0199945 A1 * | 8/2013 | Kulmala et al. | 205/780.5 |

FOREIGN PATENT DOCUMENTS

| | | |
|---|---|---|
| EP | 1892524 A1 | 2/2008 |
| JP | 6-239704 A | 8/1994 |
| JP | 2010-237020 A | 10/2010 |
| WO | 97/36931 A1 | 10/1997 |
| WO | 98/12539 A1 | 3/1998 |
| WO | 98/57154 A1 | 12/1998 |
| WO | 99/14599 A1 | 3/1999 |
| WO | 99/32662 A1 | 7/1999 |
| WO | 99/58962 A1 | 11/1999 |
| WO | 99/63347 A3 | 12/1999 |
| WO | 00/03233 A1 | 1/2000 |
| WO | 02/27317 A2 | 4/2002 |
| WO | 2006/069023 A2 | 6/2006 |
| WO | 2007/076023 A2 | 7/2007 |

OTHER PUBLICATIONS

International Preliminary Report on Patentability issued Oct. 18, 2012 in Application No. PCT/EP2011/0608540, 6 pages.

Butler, John E., "Solid Supports in Enzyme-Linked Immunosorbent Assay and Other Solid-Phase Immunoassays," Methods, 2000, pp. 4-23, vol. 22.

Kulmala, S. et al., "Electrochemiluminescent labels for applications in fully aqueous solutions at oxide-covered aluminum electrodes," Analytica Chimica Acta, 1999, pp. 1-6, vol. 386.

Liu, Xiaoqing et al., "Tris(2,2'-bipyridyl)ruthenium(II) electrochemiluminescent detection of coreactants containing aromatic diol group by the interaction between diol and borate anion," Electrochemistry Communications, 2007, pp. 2666-2670, vol. 9.

Lonberg, Nils, "Human antibodies from transgenic animals," Nature Biotechnology, Sep. 2005, pp. 1117-1125, vol. 23, No. 9.

Martin, Charles R. and Mitchell, David T., "Nanomaterials in Analytical Chemistry," Analytical Chemistry News & Features, May 1998, pp. 322A-327A, vol. 70.

Morrison, Sherie L. et al., "Chimeric human antibody molecules: Mouse antigen-binding domains with human constant region domains," Proceedings of the National Academy of Sciences USA, Nov. 1984, pp. 6851-6855, vol. 81.

Neuberger, M. S. et al., "A hapten-specific chimaeric IgE antibody with human physiological effector function," Nature, Mar. 1985, pp. 268-270, vol. 314.

Richter, Mark M., "Electrochemiluminescence (ECL)," Chemical Reviews, 2004, pp. 3003-3036, vol. 104.

Riechmann, Lutz et al., "Reshaping human antibodies for therapy," Nature, Mar. 1988, pp. 323-327, vol. 332.

* cited by examiner

USE OF SIGNAL ENHANCING COMPOUNDS IN ELECTROCHEMILUMINESCENCE DETECTION

CROSS-REFERENCE TO RELATED APPLICATIONS

This patent application is a continuation of Int. Pat. Appln. No. PCT/EP2011/068540, filed on Oct. 24, 2011; which claims the benefit of European Pat. Appln. No. EP 10188716.4, filed on Oct. 25, 2010 and European Pat. Appln. No. EP 10192106.2, filed on Nov. 22, 2010; the entire contents of these earlier filed applications are hereby incorporated by reference, for any and all purposes.

BACKGROUND

Methods for measuring electrochemiluminescent phenomena have been known for some years. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

At this time, there are a number of commercially available instruments that utilize electrochemiluminescence (ECL) for analytical measurements. Species that can be induced to emit ECL (ECL-active species) have been used as ECL labels. Examples of ECL labels include organometallic compounds such as the tris-bipyridyl-ruthenium (RuBpy) moiety where the metal is from, for example, the metals of group VII and VIII, including Re, Ru, Ir and Os. Species that react with the ECL label in the ECL process are referred to herein as ECL coreactants. Commonly used coreactants for ECL include tertiary amines (e.g., tripropylamine (TPA)), oxalate, and persulfate. The light is generated by ECL labels or ligands; the participation of the binding reagent in a binding interaction can be monitored by measuring ECL emitted from the ECL label. Alternatively, the ECL signal from an ECL-active compound may be indicative of the chemical environment (see, e.g., U.S. Pat. Nos. 5,641,623 and 5,643,713, which describes ECL assays that monitor the presence or destruction of special ECL coreactants). For more background on ECL, ECL labels, ECL assays and instrumentation for conducting ECL assays see U.S. Pat. Nos. 5,093,268; 5,147,806; 5,240,863; 5,308,754; 5,324,457; 5,591,581; 5,597,910; 5,679,519; 5,705,402; 5,731,147; 5,786,141; 5,846,485; 5,866,434; 6,066,448; 6,136,268 and 6,207,369, and European Pat. No. 0 441 875, and Int. Pat. Appln. Pub. Nos. WO 97/36931; WO 98/12539; WO 99/14599; WO 99/32662; WO 99/58962; WO 99/63347; WO 00/03233 and WO 98/57154.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells.

Available sample volumes for the determination of analytes are often limited and more and more different analytes have to be determined out of one sample. Also the development of faster laboratory equipment for assay automation and more sensitive methods for the detection of analytes are required. This leads to the need for high sensitive and specific electrochemiluminescent assays and methods for performing them. In addition, improvements associated with safety hazards or environmental concerns should be considered.

However, even more sensitive detection of analytes would be of great advantage. Thus, the present methods may provide improvements over known methods and reagent compositions, especially with respect to enhancement of the ECL signal and an improved analyte detection in combination with electrochemiluminescent procedures. It would be desirable to find novel signal enhancing reagents and/or compounds with improved performance in electrochemiluminescent assays.

SUMMARY

The application relates to methods for the detection of an analyte in a sample by electrochemiluminescence using new reagent compositions. New reagent compositions, reagent kits for measuring electrochemiluminescence (ECL) and electrochemiluminescence detection methods using the new reagent compositions are disclosed. In particular, the application relates to the use of novel combinations of compounds, which can be used in said measurements to provide improved assay performance.

The present application includes one embodiment directed to a method for measuring an analyte in a sample via electrochemiluminescent detection, comprising the steps of a) incubating the sample with a detection reagent labeled with an electrochemiluminescent group, b) separating analyte-bound and analyte-free labeled detection reagent, c) incubating the separated labeled detection reagent with a reagent composition comprising i) at least one coreactant, and ii) at least one compound selected from the group of carbonic acid amides of Formula I and Formula II,

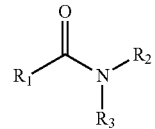

Formula I with $R_1$=$CH_3$, $CH_2F$, $CH_2Cl$, $CH_2CH_3$, $CHClCH_3$, $CH_2CH_2Cl$, $C(CH_3)_2CH_3$, $CH_2CH_2CH_3$, $CClHCH_2CH_3$ or $CH_2CH_2CH_2CH_3$, with $R_2$=H, and with $R_3$=H,

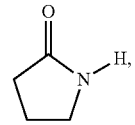

Formula II d) electrochemically triggering the release of luminescence, and e) determining the electrochemiluminescence (ECL) signal thereby measuring the analyte.

Another embodiment is directed to a method for detecting an analyte in a sample, comprising the steps of:
a) incubating the sample with a detection reagent labeled with an electrochemiluminescent group, typically to provide an analyte-bound labeled detection reagent; and
b) electrochemically triggering the release of electrochemiluminescence by the labeled detection reagent (typically an analyte-bound labeled detection reagent), which is incubated with a reagent composition which includes i) at least one ECL coreactant, such as a tertiary amine, oxalate or persulfate;
ii) at least one carbonic acid amide selected from 2-pyrrolidone and compounds having a formula

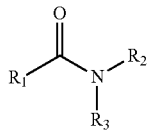

wherein $R_1$ is —H, or a $C_1$-$C_5$ alkyl group, optionally substituted with a single chlorine or fluorine atom, $R_2$=H, and $R_3$=H.

The present application also provides a reagent composition for determining ECL, comprising i) at least one ECL coreactant and ii) at least one carbonic acid amide, such as 2-pyrrolidone and/or a carbonic acid amide represented by the formula $$R_1-C(O)-NR_2R_3$$

wherein $R_1$ is —H or a $C_1$-$C_5$ alkyl group, which is optionally substituted with a single chlorine or fluorine atom, $R_2$=H, and $R_3$=H. Typically, the carbonic acid amide includes a compound(s) selected from the group of carbonic acid amides of Formula I and Formula II.

The present application also relates to a reagent mixture, comprising a reagent composition for determining ECL, which comprises i) at least one ECL coreactant, ii) at least one carbonic acid amide selected from 2-pyrrolidone and carbonic acid amides represented by the formula $$R_1-C(O)-NR_2R_3$$

wherein $R_1$ is —H or a $C_1$-$C_5$ alkyl group, which is optionally substituted with a single chlorine or fluorine atom, $R_2$=H, and $R_3$=H, iii) a sample to be investigated, and iv) at least one detecting reagent labeled with an electrochemiluminescent group ("ECL group"). Typically, the carbonic acid amide includes one or more compounds selected from the group of carbonic acid amides of Formula I and Formula II.

The present application also relates to a kit for measuring ECL, which contains a reagent composition for determining ECL, which comprises i) at least one ECL coreactant, ii) at least one carbonic acid amide selected from 2-pyrrolidone and carbonic acid amides represented by the formula $$R_1-C(O)-NR_2R_3$$

wherein $R_1$ is —H or a $C_1$-$C_5$ alkyl group, which is optionally substituted with a single chlorine or fluorine atom, $R_2$=H, and $R_3$=H. The reagent composition typically comprises the carbonic acid amide(s) in a concentration of about 0.01 M to 0.25 M. The carbonic acid amide may include a compound(s) selected from the group of carbonic acid amides of Formula I and Formula II. The reagent composition may also include boric acid and/or borate, typically in a concentration of about 0.1 to 5%.

The methods, reagents and kits disclosed herein, as well as additional objects, features and advantages thereof, will be understood more fully from the following detailed description of certain embodiments, which are intended to illustrate the methods, reagents and/or kits but the specific embodiments discussed herein are merely illustrative of specific ways to make and use the methods, reagents and/or kits and do not delimit their scope.

DETAILED DESCRIPTION

Figure 1:
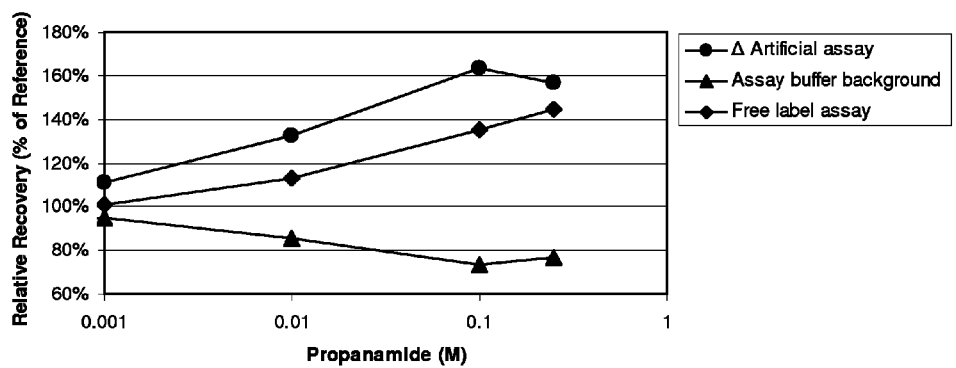
FIG. 1 depicts measurement results with propanamide concentrations of 0.001 M to 0.25 M (X-axis); relative recovery rate (% of Reference) of the measurement of ΔArtificial assay (artificial assay—assay buffer background), assay buffer background and free label assay are shown (Y-axis) as discussed in Example 1.

The practicing of the methods described herein will typically include, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Unless defined otherwise, technical and scientific terms used herein have the same meaning as commonly understood by one of ordinary skill in the art to which the methods, reagent compositions and kits described herein belong. Singleton et al., Dictionary of Microbiology and Molecular Biology, $2^{nd}$ ed., J. Wiley & Sons, New York (1994); March, Advanced Organic Chemistry Reactions, Mechanisms and Structure, 4th ed., John Wiley & Sons, New York (1992); Lewin, B., Genes V, published by Oxford University Press (1994), ISBN 0-19-854287 9); Kendrew, J. et al. (eds.), The Encyclopedia of Molecular Biology, published by Blackwell Science Ltd. (1994), ISBN 0-632-02182-9); and Meyers, R. A. (ed.), Molecular Biology and Biotechnology: a Comprehensive Desk Reference, published by VCH Publishers, Inc. (1995), ISBN 1-56081-569 8) provide one skilled in the art with a general guidance to many of the terms used in the present application. All references cited herein, including patent applications and publications, are incorporated by reference in their entirety.

DEFINITIONS

As used herein, each of the following terms has the meaning associated with it in this section.

The articles "a" and "an" are used herein to refer to one or to more than one (i.e., to at least one) of the grammatical object of the article. By way of example, "an analyte" means one analyte or more than one analyte. The term "at least" is used to indicate that optionally one or more further objects may be present. By way of example, an array comprising at least two discrete areas may optionally comprise two or more discrete test areas.

The expression "one or more" denotes 1 to 50, typically 1 to 20, also typically 2, 3, 4, 5, 6, 7, 8, 9, 10, 12, or 15.

Examples for "carbonic acid amides" and their chemical structures are listed in Table 1. The carbonic acid amides have the following common structure (as shown in Table 1), unless otherwise stated.

TABLE 1

| No. | CA Index name | CAS-No. | structure | Residues |
|---|---|---|---|---|
| 1 | formamide | 75-122-7 | 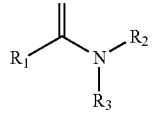 | $R_1 = H$<br>$R_2 = H$<br>$R_3 = H$ |
| 2 | acetamide | 60-35-5 | see above | $R_1 = CH_3$<br>$R_2 = H$<br>$R_3 = H$ |
| 3 | 2-fluoroacetamide | 640-19-7 | see above | $R_1 = CH_2F$<br>$R_2 = H$<br>$R_3 = H$ |
| 4 | 2,2,2-trifluoroacetamide | 354-38-1 | see above | $R_1 = CF_3$<br>$R_2 = H$<br>$R_3 = H$ |
| 5 | 2-chloroacetamide | 79-07-2 | see above | $R_1 = CH_2Cl$<br>$R_2 = H$<br>$R_3 = H$ |
| 6 | 2,2-dichloroacetamide | 68372-7 | see above | $R_1 = CHCl_2$<br>$R_2 = H$<br>$R_3 = H$ |
| 7 | 2-bromoacetamide | 683-57-8 | see above | $R_1 = CH_2Br$<br>$R_2 = H$<br>$R_3 = H$ |
| 8 | 2-jodoacetamide | 144-48-9 | see above | $R_1 = CH_2J$<br>$R_2 = H$<br>$R_3 = H$ |
| 9 | 2-hydroxyacetamide | 598-42-5 | see above | $R_1 = CH_2OH$<br>$R_2 = H$<br>$R_3 = H$ |
| 10 | Acetoacetamide | 5977-14-0 | see above | $R_1 = CH_2COCH_3$<br>$R_2 = H$<br>$R_3 = H$ |
| 11 | 2-chloro-N,N-dimethylacetamide | 2675-89-0 | see above | $R_1 = CH_2Cl$<br>$R_2 = CH_3$<br>$R_3 = CH_3$ |
| 12 | 2-chloro-N-hydroxy-methylacetamide | 2832-19-1 | see above | $R_1 = CH_2Cl$<br>$R_2 = CH_2OH$<br>$R_3 = H$ |
| 13 | 2-chloro-N-methoxy-N-methylacetamide | 67442-07-3 | see above | $R_1 = CH_2Cl$<br>$R_2 = CH_3$<br>$R_3 = OCH_3$ |
| 14 | propanamide (propionamide) | 79-05-0 | see above | $R_1 = CH_2CH_3$<br>$R_2 = H$<br>$R_3 = H$ |
| 15 | 2-chloropropanamide | 27816-36-0 | see above | $R_1 = CHClCH_3$<br>$R_2 = H$<br>$R_3 = H$ |
| 16 | 3-chloropropanamide | 5875-24-1 | see above | $R_1 = CH_2CH_2Cl$<br>$R_2 = H$<br>$R_3 = H$ |
| 17 | N-methylpropanamide | 1187-58-2 | see above | $R_1 = CH_2CH_3$<br>$R_2 = CH_3$<br>$R_3 = H$ |
| 18 | 2,2-dimethyl-propanamide | 754-10-9 | see above | $R_1 = C(CH_3)_2CH_3$<br>$R_2 = H$<br>$R_3 = H$ |
| 19 | propanediamide | 108-13-4 | see above | $R_1 = CH_2CONH_2$<br>$R_2 = H$<br>$R_3 = H$ |
| 20 | Butanamide | 541-35-5 | see above | $R_1 = CH_2CH_2CH_3$<br>$R_2 = H$<br>$R_3 = H$ |

TABLE 1-continued

| No. | CA Index name | CAS-No. | structure | Residues |
|---|---|---|---|---|
| 21 | 2-chlorobutanamide | 2455-04-1 | see above | $R_1$ = CClHCH$_2$CH$_3$<br>$R_2$ = H<br>$R_3$ = H |
| 22 | Pentanamide | 626-97-1 | see above | $R_1$ = CH$_2$CH$_2$CH$_2$CH$_3$<br>$R_2$ = H<br>$R_3$ = H |
| 23 | Hexanamide | 628-02-4 | see above | $R_1$ = CH$_2$CH$_2$CH$_2$CH$_2$CH$_3$<br>$R_2$ = H<br>$R_3$ = H |
| 24 | 2-pyrrolidinone | 616-45-5 | 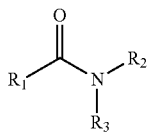 | |
| 25 | 2,5-butanimide | 123-56-8 | 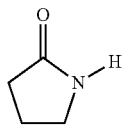 | |

Formula I as used herein denotes with $R_1$=H, CH$_3$, CH$_2$F, CH$_2$Cl, CH$_2$CH$_3$, CHClCH$_3$, CH$_2$CH$_2$Cl, C(CH$_3$)$_2$CH$_3$, CH$_2$CH$_2$CH$_3$, CClHCH$_2$CH$_3$ or CH$_2$CH$_2$CH$_2$CH$_3$, with $R_2$=H, and with $R_3$=H. In certain embodiments where $R_1$=CH$_2$Cl, $R_2$ and $R_3$ may be selected such that one of these substituents is CH$_3$ and the other is H or CH$_3$.

Formula II as used herein denotes to the following structure named 2-pyrrolidinone, represented in Table 1 as No. 24.

The embodiments of the methods, reagents and kits disclosed herein can be used to test a variety of samples which may contain an analyte or activity of interest. Such samples may be in solid, emulsion, suspension, liquid, or gas form. They may be, but are not limited to, samples containing or derived from human or animals, for example, cells (live or dead) and cell-derived products, immortalized cells, cell fragments, cell fractions, cell lysates, organelles, cell membranes, hybridoma, cell culture supernatants (including supernatants from antibody producing organisms such as hybridomas), waste or drinking water, food, beverages, pharmaceutical compositions, blood, serum, plasma, hair, sweat, urine, feces, stool, saliva, tissue, biopsies, effluent, separated and/or fractionated samples, separated and/or fractionated liquids, organs, plants, plant parts, plant byproducts, soil, water, water supply, water sources, filtered residue from fluids (gas and liquid), swipes, absorbent materials, gels, cytoskeleton, unfractionated samples, unfractionated cell lysates, cell nucleus/nuclei, nuclear fractions, chemicals, chemical solutions, structural biological components, skeletal (ligaments, tendons) components, separated and/or fractionated skeletal components, hair fractions and/or separations, skin, skin samples, skin fractions, dermis, endodermis, eukaryotic cells, prokaryotic cells, fungus, yeast, immunological cells, drugs, therapeutic drugs, oils, extracts, mucous, sewage, environmental samples, organic solvents or air. In an embodiment the sample can further comprise, for example, water, alcohols, acetonitrile, dimethyl sulfoxide, dimethyl formamide, n-methyl-pyrrolidone, methanol or other organic solvents.

A "sample" as used herein is obtained for the purpose of an evaluation in vitro. As the skilled artisan will appreciate, any such assessment is made in vitro. If the sample is a patient sample, it is discarded afterwards. The patient sample is solely used for the in vitro diagnostic method disclosed herein and the material of the patient sample is not transferred back into the patient's body.

Analytes that may be measured include, but are not limited to, whole cells, cell surface antigens, protein complexes, cell signaling factors and/or components, second messengers, second messenger signaling factors and/or components, subcellular particles (e.g., organelles or membrane fragments), viruses, prions, dust mites or fragments thereof, viroids, immunological factors, antibodies, antibody fragments, antigens, haptens, fatty acids, nucleic acids (and synthetic analogs), ribosomes, proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, nucleic acid processing enzymes (e.g., polymerases, nucleases, integrases, ligases, helicases, telomerases, etc.), protein processing enzymes (e.g., proteases, kinases, protein phophatases, ubiquitin-protein ligases, etc.), cellular metabolites, endocrine factors, paracrine factors, autocrine factors, cytokines, hormones, pharmacological agents, drugs, therapeutic drugs, synthetic organic molecules, organometallic molecules, tranquilizers, barbiturates, alkaloids, steroids, vitamins, amino acids, sugars, lectins, recombinant or derived proteins, biotin, avidin, streptavidin, or inorganic molecules present in the sample.

Whole cells may be animal, plant, or bacteria, and may be viable or dead. Examples include plant pathogens such as fungi and nematodes. The term "subcellular particles" is meant to encompass, for example, subcellular organelles, membrane particles as from disrupted cells, fragments of cell walls, ribosomes, multi-enzyme complexes, and other particles which can be derived from living organisms. Nucleic acids include, for example, chromosomal DNA, plasmid DNA, viral DNA, and recombinant DNA derived from multiple sources. Nucleic acids also include RNA's, for example messenger RNA's, ribosomal RNA's and transfer RNA's. Polypeptides include, for example, enzymes, transport proteins, receptor proteins, and structural proteins such as viral coat proteins. Typical polypeptides are enzymes and antibodies. Particularly typical polypeptides are monoclonal antibodies. Hormones include, for example, insulin and T4 thyroid hormone. Pharmacological agents include, for example, cardiac glycosides. It is of course within the scope of the methods disclosed herein to include synthetic substances which chemically resemble biological materials, such as synthetic polypeptides, synthetic nucleic acids, and synthetic membranes, vesicles and liposomes. The foregoing is not intended to be a comprehensive list of the biological substances suitable for use in the present methods, but is meant only to illustrate the wide scope thereof.

Also, typically, the analyte of interest is present at a concentration of $10^{-3}$ molar or less, for example, at least as low as $10^{-18}$ molar.

The term "analyte specific reagent" (ASR) according to the present methods and reagents has to be understood as a molecule or biomolecule (e.g., a protein or antibody) with the capability to specifically bind the analyte. "Analyte specific reagents" (ASRs) are a class of biological molecules which can be used to identify and measure the amount of an individual chemical substance in biological specimens. ASRs are for example antibodies, both polyclonal and monoclonal, specific receptor proteins, ligands, nucleic acid sequences, and similar reagents which, through specific binding or chemical reaction with substances in a specimen, are intended for use in a diagnostic application for identification and quantification of an individual chemical substance or ligand in biological specimens. In simple terms an analyte specific reagent is the active ingredient of an assay. An ASR will fulfill both, the criteria for affinity as well as for specificity of binding the analyte.

The term "antibody" is used in the broadest sense and specifically covers monoclonal antibodies (including full length monoclonal antibodies), polyclonal antibodies, multi-specific antibodies (e.g., bispecific antibodies), and antibody fragments. The term "antibody" encompasses the various forms of antibody structures including whole antibodies and antibody fragments. The antibody according to the application is in one embodiment a human antibody, a humanized antibody, a chimeric antibody, an antibody derived from other animal species like mouse, goat or sheep, a monoclonal or polyclonal antibody, or a T cell antigen depleted antibody. Genetic engineering of antibodies is e.g., described in Morrison, S. L., et al., Proc. Natl. Acad. Sci. USA 81 (1984) 6851-6855; U.S. Pat. Nos. 5,202,238 and 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

Any antibody fragment retaining the above criteria of a analyte specific reagent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of antibodies and hence their performance in immunoassays can be enhanced (Tijssen, P., supra, pages 108-115).

A "detection reagent" according to the present application comprises an analyte specific reagent (ASR) labeled with an electrochemiluminescent group, or an analyte homolog labeled with an electrochemiluminescent group. According to the test format it is known to the skilled artisan, which detection reagent has to be selected for the various assay formats (e.g., sandwich assay, double antigen bridging assay (DAGS), competitive assay, homogeneous assay, heterogeneous assay). A detection reagent in a heterogeneous immunoassay might be for example an antibody. It is known to a person skilled in the art that the detection reagent can be immobilized on a solid phase. In an embodiment the method for measuring an analyte in a sample via electrochemiluminescent detection can be performed as a homogeneous assay. In an embodiment the method can be performed as a heterogeneous assay. In an embodiment the method can be performed in a sandwich assay format. In an embodiment the method can be performed in a competitive assay format. Also in an embodiment the method can be performed in a double antigen bridging assay format (DAGS). Known immunoassay formats are described in detail in the book of Price, C. P. and Newman, D. J., Principles and Practice of Immunoassay, 2nd ed. (1997).

The term "label" as used herein refers to any substance that is capable of producing a detectable signal, whether visibly or by using suitable instrumentation. Various labels suitable for use in the present methods and reagents include, but are not limited to, chromogens, fluorescent, chemiluminescent or electrochemiluminescent compounds, catalysts, enzymes, enzymatic substrates, dyes, colloidal metallic and non-metallic particles, and organic polymer latex particles.

The term "luminescence" refers to any emission of light that does not derive energy from the temperature of an energy source (for example, a source of electromagnetic radiation, a chemical reaction, mechanical energy). In general, the source causes an electron of an atom to move from a lower energy state into an "excited" higher energy state; then the electron releases that energy in the form of emitted light when it falls back to a lower energy state. Such emission of light usually occurs in the visible or near-visible range of the electromagnetic spectrum. The term "luminescence" includes, but is not limited to, such light emission phenomena such as phosphorescence, fluorescence, bioluminescence, radioluminescence, electroluminescence, electrochemiluminescence and thermo-luminescence.

The term "luminescent label" refers to a label that generates a luminescent signal, e.g., an emission of light that does not derive energy from the temperature of the emitting source. The luminescent label may be, for example, a fluorescent molecule, a phosphorescent molecule, a radioluminescent molecule, a luminescent chelate, a phosphor or phosphor-containing compound, or a quantum dot.

An "electrochemiluminescence assay" or "ECLA" is an electrochemical assay in which bound analyte molecule is detected by a label linked to a detecting agent (target molecule). An electrode electrochemically initiates luminescence of a chemical label linked to a detecting agent. Light emitted by the label is measured by a photodetector and indicates the presence or quantity of bound analyte molecule/target molecule complexes. ECLA methods are described, for example, in U.S. Pat. Nos. 5,543,112; 5,935,779; and 6,316,607. Signal modulation can be maximized for different analyte molecule concentrations for precise and sensitive measurements.

In an ECLA procedure microparticles can be suspended in the sample to efficiently bind to the analyte. For example, the particles can have a diameter of 0.05 µm to 200 µm, 0.1 µm to 100 µm, or 0.5 µm to 10 µm, and a surface component capable of binding an analyte molecule. In one frequently used ECLA-system (Elecsys®, Roche Diagnostics, Germany), the microparticles have a diameter of about 3 µm. The microparticles can be formed of crosslinked starch, dextran, cellulose, protein, organic polymers, styrene copolymer such as styrene/butadiene copolymer, acrylonitrile/butadiene/styrene copolymer, vinylacetyl acrylate copolymer, vinyl chloride/acrylate copolymer, inert inorganic particles, chromium dioxide, oxides of iron, silica, silica mixtures, proteinaceous matter, or mixtures thereof, including but not limited to sepharose beads, latex beads, shell-core particles, and the like. The microparticles are typically monodisperse, and can be magnetic, such as paramagnetic beads. See, for example, U.S. Pat. Nos. 4,628,037; 4,965,392; 4,695,393; 4,698,302; and 4,554,088. Microparticles can be used in an amount ranging from about 1 to 10,000 µg/ml, typically 5 to 1,000 µg/ml.

The expression "of interest" denotes an analyte or substance of possible relevance that shall be analyzed or determined.

"Detection" includes any means of detecting, including direct and indirect detection. The term "detection" is used in the broadest sense to include both qualitative and quantitative measurements of an analyte, herein measurements of an analyte. In one aspect, a detection method as described herein is used to identify the mere presence of an analyte of interest in a sample. In another aspect, the method can be used to quantify an amount of analyte in a sample.

To "reduce" or "inhibit" is to decrease or reduce an activity, function, and/or amount as compared to a reference. By reduce or inhibit is meant the ability to cause an overall decrease typically of 10% or greater, more typically of 25% or greater, and most typically of 50%, 75%, 90%, 95%, or greater.

To "enhance", e.g., to "enhance specific signals" or "the enhancement of ECL signals", is to increase or rise an activity, function, and/or amount as compared to a reference. By increase or rise is meant the ability to cause an overall increase typically of 10% or greater, more typically of 25% or greater, and most typically of 50% or greater.

The term "determining" is used here for both qualitative and quantitative detection of an analyte, and can include determination of the amount and/or concentration of the analyte.

The term "measuring"/"measurement" in science is the process of estimating or determining the magnitude of a quantity, such as length or mass, relative to a unit of measurement, such as a meter or a kilogram. Measuring/measurement uses a reference point against which other things can be evaluated. The term measurement can also be used to refer to a specific result (determined values) obtained from a measurement process. It is a basis for comparison. The skilled artisan is aware of materials and methods to correlate measured signals or determined values to concentrations.

A "reagent composition" or "ECL-reagent composition" according to the present application comprises reagents supporting ECL-signal generation, e.g., a coreactant, a buffering agent for pH control, and optionally other components. The skilled artisan is aware of components to be present in a reagent composition which are required for ECL signal generation in electrochemiluminescent detection methods.

An "aqueous solution" as used herein is a homogeneous solution of particles, substances or liquid compounds dissolved in water. An aqueous solution may also comprise organic solvents. Organic solvents are known to the person skilled in the art, e.g., methanol, ethanol or dimethylsulfoxid. As used herein it is also to be understood that an aqueous solution can comprise at most 50% organic solvents.

A species that participates with the ECL label in the ECL process is referred to herein as ECL "coreactant". Commonly used coreactants for ECL include tertiary amines (e.g., tripropylamine (TPA)), oxalate, and persulfate. The skilled artisan is aware of available coreactants useful for electrochemiluminescent detection methods.

A "solid phase", also known as "solid support", is insoluble, functionalized, polymeric material to which library members or reagents may be attached or covalently bound (often via a linker) to be immobilized or allowing them to be readily separated (by filtration, centrifugation, washing etc.) from excess reagents, soluble reaction by-products, or solvents. Solid phases for the methods described herein are widely described in the state of the art (see, e.g., Butler, J. E., Methods 22 (2000) 4-23). The term "solid phase" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes, chips or other spectrometer sample containers. A solid phase component of an assay is distinguished from inert solid surfaces with which the assay may be in contact in that a "solid phase" contains at least one moiety on its surface, which is intended to interact with the capture antibody or capture molecule. A solid phase may be a stationary component, such as a tube, strip, cuvette, chip or microtiter plate, or may be non-stationary components, such as beads and microparticles. Microparticles can also be used as a solid phase for homogeneous assay formats. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features (1998) 322A-327A, which is incorporated herein by reference.

The terms "chip", "bio-chip", "polymer-chip" or "protein-chip" are used interchangeably and refer to a collection of a large number of probes, markers or biochemical markers arranged on a shared substrate (e.g., a solid phase) which could be a portion of a silicon wafer, a nylon strip, a plastic strip, or a glass slide.

Methods:

In an embodiment the present application concerns a method for measuring an analyte in a sample via electrochemiluminescent detection, comprising the steps of a) incubating the sample with a detection reagent labeled with an electrochemiluminescent group, b) separating analyte-bound and analyte-free labeled detection reagent, c) incubating the separated labeled detection reagent with a reagent composition comprising i) at least one coreactant, and ii) at least one compound selected from the group of carbonic acid amides of Formula I and Formula II, Formula I

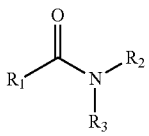

with $R_1$=with $R_1$=$CH_3$, $CH_2F$, $CH_2Cl$, $CH_2CH_3$, $CHClCH_3$, $CH_2CH_2Cl$, $C(CH_3)_2CH_3$, $CH_2CH_2CH_3$, $CClHCH_2CH_3$ or $CH_2CH_2CH_2CH_3$, with $R_2$=H, and with $R_3$=H, Formula II

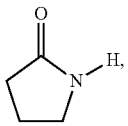

d) electrochemically triggering the release of luminescence, and e) determining the electrochemiluminescence (ECL) signal thereby measuring the analyte.

Another aspect of the application provides improved ECL methods based on the reagent compositions of the present application, particularly ECL methods featuring low detection limits. The reagent compositions surprisingly enhance specific signals and reduce background signals. More specifically, the methods of the application provide improved sensitivity at low detection levels by reducing the background electrochemiluminescence in the absence of ECL labels.

The methods and reagents described in this application surprisingly illustrate that the use of certain compounds from the group of carbonic acid amides can provide a number of advantages including improved signal generation in ECL detection methods and thus improved ECL assay performance.

A feature of this application may include methods for the determination of an analyte in a sample to be investigated using an electrochemiluminescent label, wherein one of the following listed methods for measuring electrochemiluminescent phenomena is employed.

Surprisingly the methods using compounds selected from the group of carbonic acid amides emit less background luminescence than conventional test reagents without these compounds. This is particularly an advantage at low detection levels where increasing the signal to background ratio (=signal to noise ratio) greatly improves the sensitivity. Surprisingly, it has been found that performing an electrochemiluminescent detection using a method according to the present application can result in a 10% to 60% improved signal to noise ratio of ECL detection.

The method for measuring an analyte in a sample via electrochemiluminescent detection according to the present application can be performed in an embodiment in an aqueous solution.

In an embodiment, the carbonic acid amide used in the method may be selected from the group consisting of acetamide, 2-fluoroacetamide, 2-chloroacteamide, propanamide, 2-chloropropanamide, 3-chloropropanamide, butanamide and 2-chlorobutanamide.

In a typical embodiment, the carbonic acid amide used in the method is selected from the group consisting of acetamid, 2-chloroacetamide, propanamide and butanamide.

In another typical embodiment, the carbonic acid amide used in the method is selected from the group consisting of acetamid, propanamide and butanamide.

In a typical embodiment, the carbonic acid amide may be used in the method in a concentration of 0.01 M to 0.25 M. In a further typical embodiment, the carbonic acid amide may be used in a concentration of 0.01 M to 0.2 M. In a further typical embodiment, the carbonic acid amide may be used in a concentration of 0.01 M to 0.1 M.

In an embodiment, the method according to the present application may be particularly well suited to detect biomolecules, such as proteins, polypeptides, peptides, peptidic fragments, hormones, peptide hormones, vitamins, provitamins, vitamin metabolites and amino acids in a sample of interest.

The sample used in the methods according to the present application may be in an embodiment a liquid sample, e.g., whole blood, serum or plasma. The sample, or more specific the sample of interest, in an embodiment may comprise any body fluid and stool. In an embodiment the sample will be a liquid sample like saliva, stool extracts, urine, whole blood, plasma or serum. In an embodiment the sample will be whole blood, plasma or serum.

It is known to a person skilled in the art that steps "a) incubating the sample with a detection reagent labeled with an electrochemiluminescent group" and "b) separating analyte-bound and analyte-free labeled detection reagent" in the method might be performed in the same location, e.g., in the same reaction vessel. Said steps (a) and (b) might be performed in an automatic process controlled by an appropriate device.

Unspecific sample components and analyte-free labeled detection reagent can be removed in step (b) according to the method in a separation process. For example that analyte-bound and analyte-free labeled detection reagent can be separated using a washing step.

Also other test components supporting the electrochemiluminescent detection of an analyte may be used in the methods according to the present application.

An aspect of the methods, reagents and kits disclosed herein relates to the need for effective preservation, e.g., for long term storage of reagent mixtures and reagent compositions. Suitable preservatives should have no effect on ECL signal generation or in an ideal case a positive influence on ECL signal generation.

As suitable preservative compounds boric acid and/or borate were identified that effectively control bacterial and fungal growth and surprisingly increase the specific ECL signals. An ECL detection method using a reagent composition comprising boric acid and/or borate as preservative has the positive surprising effect of an increase in the specific ECL signal generated.

In one embodiment, the present method for measuring an analyte in a sample via electrochemiluminescent detection, comprises the steps of a) incubating the sample with a detection reagent labeled with an electrochemiluminescent group, b) separating analyte-bound and analyte-free labeled detection reagent, c) incubating the separated labeled detection reagent with a reagent composition comprising i) at least one coreactant, and ii) a preservative selected from the group consisting of boric acid and/or borate, d) electrochemically triggering the release of luminescence, and e) determining the electrochemiluminescence (ECL) signal thereby measuring the analyte.

In an embodiment, the method for measuring an analyte in a sample via electrochemiluminescent detection is characterized in that the reagent composition for ECL signal generation comprises a preservative selected from the group consisting of boric acid and/or borate at a concentration of 0.1% to 5%, typically at a concentrations of 0.5% to 4%, and more typically at a concentration of 0.5% to 2%.

In an embodiment, the method for measuring an analyte in a sample via electrochemiluminescent detection is characterized in that the reagent composition for ECL signal generation comprises boric acid as preservative at concentrations of 0.1% to 5%, typically at concentrations of 0.5% to 4%, and more typically at concentrations of 0.5% to 2%.

In an embodiment, the method for measuring an analyte in a sample via electrochemiluminescent detection is characterized in that the reagent composition for ECL signal generation comprises boric acid and/or borate as preservative at concentrations of 0.1% to 5%, typically at concentrations of 0.5% to 4%, and more typically at concentrations of 0.5% to 2%.

It has been found that a method for measuring an analyte in a sample via electrochemiluminescent detection combining the effect of carbonic acid amides and boric acid and/or borate in one reagent composition can result in a further improved signal to noise ratio in ECL detection. The accumulated effect of carbonic acid amides and boric acid and/or borate in one reagent composition leads to at least 10%, 25% or 50% improved signal generation in ECL detection.

In another embodiment, the present application provides a method for measuring an analyte in a sample via electrochemiluminescent detection, comprising the steps of a) incubating the sample with a detection reagent labeled with an electrochemiluminescent group, b) separating analyte-bound and analyte-free labeled detection reagent, c) incubating the separated labeled detection reagent with a reagent composition comprising i) at least one coreactant, ii) at least one compound selected from the group of carbonic acid amides of Formula I and Formula II and iii) at least one preservative selected from the group of boric acid and/or borate, d) electrochemically triggering the release of luminescence, and e) determining the electrochemiluminescence (ECL) signal thereby measuring the analyte.

In an embodiment, the method for measuring an analyte in a sample via electrochemiluminescent detection is characterized in that the reagent composition comprises in addition a detergent and a buffering agent.

In an embodiment, the method for measuring an analyte in a sample via electrochemiluminescent detection is characterized in that the reagent composition comprises in addition a salt and/or an anti-foam agent.

In an embodiment, the present application provides a method for conducting an electrochemiluminescence assay wherein electrochemiluminescence is induced in the presence of a reagent composition.

A typical ECL measurement process for an ECL immunoassay comprises multiple exchanges of liquids and/or mixtures in the ECL measurement cell (e.g., a flow cell). A typical ECL measurement process consists of several steps explained below.

The skilled artisan is aware that an ECL measurement cell has to be conditioned or regenerated before the ECL detection step takes place by rinsing said ECL measurement cell with a reagent composition according to the present application and additional the application of an electric potential. This step is one part of the process of determining analytes using ECL. It has been described in European Pat. No. 1 051 621 that during this conditioning step a layer is formed on the surface of the measurement electrode(s) supporting the signal generation during the measurement of an analyte in an ECL measurement cell.

For a typical ECL measurement process, a reagent mixture is induced into the cleaned and conditioned ECL measurement cell through the fluid inlet channel into the ECL measurement cell cavity. This mixture is an incubate of the sample, reagents and magnetic particles. Said mixture induced into the measurement cell may be surrounded by a reagent composition according to the present application flowing in front and after said mixture.

In such an ECL immunoassay, a detection reagent comprising complex-molecules which are labeled with an electrochemiluminescent group and which are characteristic for the analysis, are bound to these magnetic particles by a pair of specific biochemical binding partners, e.g., streptavidin and biotin. The magnetic particles are for example coated with streptavidin-polymer, whereas biotin is bound to the complex-molecules.

In the ECL measurement cell the magnetic particles are trapped to the surface of an electrode together with the labeled complex-molecules bound thereto in the magnetic field of a magnet arranged close to said electrode. The magnetic field is applied during a continuous flow of the mixture, whereby incubate and/or reagent composition discharges from the ECL measurement cell cavity through the fluid outlet channel.

After trapping the magnetic particles, a reagent composition according to the present application containing an ECL coreactant is induced into the ECL measurement cell in a next step, whereby the magnetic particles are washed by said reagent composition. This step of washing is to remove unbound components of said incubate from the electrode which potentially interfere with the electrochemical reaction.

Thereafter the release of the electrochemiluminescence (ECL) signal is electrochemically triggered by application of an electric potential, whereby the intensity of the luminescence light is detected by means of a photosensor and may be evaluated as a measure for the concentration of the labeled complex-molecules on the magnetic particles located at the surface of the electrode, whereby this concentration again serves as a measure for the concentration of the analyte in the sample.

After the electrochemiluminescence detection the ECL measurement cell usually is rinsed with a cleaning fluid.

An apparatus for carrying out detection methods by means of electrochemiluminescence is mentioned in the example section (Example 1, 2 or 3) or described in European Pat. No. 1 892 524 (A1). Moreover, such an apparatus can comprise means for controlling the temperature of the measuring unit and/or a liquid vessel. The measuring unit is understood to be a cell in which the electrochemiluminescence is measured. The liquid vessel can be a storage container, but also a feeding device; for example, a tube for the reagent solution, contained in the measuring unit during the measurement.

Compositions

Another aspect of the present methods, reagents and kits relates to an improved reagent composition for ECL-signal generation, which leads to enhanced signal to noise ratios. More specifically, the reagent composition of the present application provides improved sensitivity at low detection levels by reducing the background electrochemiluminescence in the absence of ECL labels. Surprisingly a reagent composition comprising compounds like carbonic acid amides emit less background luminescence than conventional test reagents without these compounds. This is particularly an advantage at low detection levels where increasing the signal to background ratio (=signal to noise ratio) greatly improves the sensitivity. This improved reagent composition contains a compound from the group of carbonic acid amides as well as other compounds supporting the method for generating ECL. Surprisingly it has been found that performing an electrochemiluminescent detection using a reagent composition according to the present application can result in a 10% to 60% improved signal to noise ratio of ECL detection.

An aspect of the present methods, reagents and kits relates to a reagent composition that gives high signal to background ratios in electrochemiluminescence assays. The signal difference between specific signals and background signals is increased. Such improved properties have been achieved through the identification of advantageous combinations of ECL coreactant, pH buffering agents, detergent and pH and, in particular, through the use of compounds selected from group consisting of carbonic acid amides.

The reagent composition provides a suitable environment for efficiently inducing ECL labels to emit ECL and for sensitively measuring ECL labels via the measurement of ECL. The reagent composition of the application may optionally comprise additional components including preservatives, detergents, anti-foaming agents, ECL active species, salts, acidic and basic compounds for pH control (buffering agents), metal ions and/or metal chelating agents. The reagent composition of the application may also include components of a biological assay, which in some cases may be labeled with an ECL label, including binding reagents, enzymes, enzyme substrates, cofactors and/or enzyme inhibitors. The present application also provides assay reagents, compositions, kits, systems and system components that comprise the reagent composition described herein and, optionally, additional assay components. The present application also provides methods for conducting ECL assays using the reagent composition described herein.

In an embodiment the present application provides a reagent composition for determining ECL, comprising i) a compound selected from the group of carbonic acid amides of Formula I and Formula II, and ii) at least one coreactant.

In an embodiment, the carbonic acid amide of the reagent composition is selected from the group consisting of acetamide, 2-fluoroacetamide, 2-chloroacteamide, propanamide, 2-chloropropanamide, 3-chloropropanamide, butanamide and 2-chlorobutanamide.

In a typical embodiment, the carbonic acid amide is selected from the group consisting of acetamid, 2-chloroacetamide, propanamide and butanamide. In a further embodiment the carbonic acid amide is selected from the group consisting of acetamid, propanamide and butanamide. Carbonic acid amides have individual concentration optima for the ECL enhancing effect. As shown in the experiments (especially table 2, 3 and 4) the skilled artisan is aware to select the appropriate concentration for the selected carbonic acid amide in the reagent composition. Methods to determine the optimal concentration for a carbonic acid amide in the reagent composition is known to the skilled artisan.

In an embodiment, the reagent composition comprises the carbonic acid amides in a concentration of 0.01 M to 0.25 M. In a further embodiment the reagent composition comprises the carbonic acid amides in a concentration of 0.01 M to 0.2 M. In a further embodiment the reagent composition comprises the carbonic acid amides in a concentration of 0.01 M to 0.1 M.

The coreactant of the reagent composition in an embodiment is selected from the group of tertiary amines (e.g., tripropylamine (TPA)), oxalate, and persulfate. In a typical embodiment the coreactant is TPA.

It may be beneficial when storing a reagent composition to include a preservative that prevents microbial growth. Additionally, suitable preservatives are identified to control bacterial and fungal growth to enable long term storage and use of the reagent composition. The reagent composition according to the present application may additionally contain one or more preservatives. In an embodiment of the present application, the reagent composition comprises a preservative (preservative agent).

In an embodiment, the present application provides a reagent composition for determining ECL, comprising i) a compound selected from the group of carbonic acid amides of Formula I and Formula II, ii) at least one coreactant, and iii) at least one preservative.

Typically, the preservative has no or a positive effect on ECL signal generation. It is known to a person skilled in the art, that oxazolidines (e.g., Oxaban A or 4,4 dimethyl oxazolidine), azide and related preservatives are compatible with ECL. Oxazolidines at concentrations of 0.01% to 1% are normally used in test reagents. In an embodiment the reagent composition comprises preservatives selected from the group of Oxazolidines, typically Oxaban A. In an embodiment, the reagent composition comprises preservatives in a concentration of 0.01% to 1%, in another embodiment the reagent composition comprises preservatives in a concentration of 0.1% to 1%. It might also be beneficial to use a mixture of two or more preservatives.

The carbonic acid amide 2-chloroacetamide (CAA), as already mentioned above, has in addition to its ECL signal enhancing effect also a preservative function.

As mentioned above, an aspect of the present application provides for adding an effective preservative that has no or a positive influence on ECL signal generation. As suitable inorganic compounds boric acid and/or borate were identified that effectively control bacterial and fungal growth. Surprisingly, it has been found that boric acid and/or borate present in a reagent composition for determining ECL have no negative influence in ECL signal generation. It has surprisingly been found that a reagent composition comprising boric acid and/or borate as preservative has a positive effect on the ECL signal generation process, namely an increase of the specific signal. Additionally their high activity and low degree of problems associated with safety hazards or environmental concerns are advantageous. Boric acid and/or borate, is contrary to some other commonly used preservatives in reagent compositions, halogen free and does not release formaldehyde. Results with boric acid and borate present in ECL signal generation are shown in the example section, e.g., Example 2.

In an embodiment, the present application provides a reagent composition for determining ECL, comprising i) at least one coreactant, and ii) at least one preservative selected from the group consisting of boric acid, borate and mixtures thereof.

In an embodiment, the present application provides a reagent composition for determining ECL, comprising i) at least one coreactant, and ii) the preservative boric acid.

In an embodiment, the present application provides a reagent composition for determining ECL, comprising i) at least one coreactant, and ii) the preservative borate.

In an embodiment, the present application provides a reagent composition for determining ECL, comprising i) a compound selected from the group of carbonic acid amides of Formula I and Formula II, ii) at least one coreactant, iii) at least one preservative selected from the group consisting of boric acid, borate and mixtures thereof.

In an embodiment, the reagent composition according to the present application comprises boric acid and/or borate as preservative in a concentration of 0.1% to 5%, typically in a concentration of 0.5% to 4%, and particularly typically in a concentration of 0.5% to 2%.

In a typical embodiment, the reagent composition according to the present application comprises boric acid as preservative at concentrations of 0.1% to 5%, typically in a concentration of 0.5% to 4%, and particularly typically in a concentration of 0.5% to 2%.

In a typical embodiment, the reagent composition according to the present application comprises borate as preservative at concentrations of 0.1% to 5%, typically in a concentration of 0.5% to 4%, and particularly typically in a concentration of 0.5% to 2%.

The reagent composition according to the present application optionally comprises in addition other test components. Other test components are selected from the group consisting of at least one detergent, at least one signal enhancing compound, buffering agents comprising acidic and basic agents for pH control, and water.

In an embodiment, the current application relates to a reagent composition for determining ECL comprising i) a compound selected from the group of carbonic acid amides of Formula I and Formula II, ii) at least one coreactant, iii) at least one preservative, iv) buffering agents, v) at least one detergent, vi) a salt and/or anti-foam agent, and vii) optionally other test components.

Suitable detergents for a reagent composition according to the present application are those from the group consisting of fatty acid alcohol ethoxylates, including poly(ethylene glycol)ethers, for example polidocanol or other poly(ethylene glycol)ethers with the formula $C_xEO_y$ with X=8-18 and Y=2-9, genapol (isotridecylpoly((ethylene glycol ether)$_n$), Plantaren® (alkylpolyglucoside), octylglucoside (octyl-beta-D-glucopyranoside) as well as zwitterionic detergents like Zwittergent 3-12 or a mixture thereof. The detergents are used in concentrations ranging between 0.01% and 2%. The optimal concentration can be easily determined for each detergent. The most suitable concentrations are those ranging between 0.05% and 1%.

In an embodiment, the reagent composition according to the present application comprises detergents selected from the group consisting of polidocanol or other poly(ethylene glycol)ethers with the formula $C_xEO_y$ with X=8-18 and Y=2-9, octylglucoside (octyl-beta-D-glucopyranoside) or zwitterionic detergents like Zwittergent 3-12 or a mixture thereof. In a typical embodiment the reagent composition comprises detergents selected from the group consisting of polidocanol, octylglucoside (octyl-beta-D-glucopyranoside) and Zwittergent 3-12, or a mixture thereof.

Further the electrochemiluminescent signal can also be increased by adjusting the pH to a value between 6.0 and 8.0, typically between 6.0 and 7.5, particularly typically between 6.2 and 6.9. This can be done conventionally by using a pH buffering agent suitable for this range, known to a person skilled in the art. In an embodiment the buffering agent suitable for the reagent composition comprises KOH and phosphoric acid ($H_3PO_4$).

Furthermore, the signal can be increased by adding salts, including inorganic salts like, for example, NaBr, NaCl, NaJ. The salts, especially NaCl, are added in concentrations ranging between 1 mM and 1 M, typically between 10 mM and 100 mM, and most typically between 10 mM and 50 mM.

It may be beneficial, especially in HTS applications, to avoid the production of bubbles or foam. For this reason it may be desirable to add anti-foaming agents to a reagent composition. Many commercial antifoaming agents (including Antifoams o-30, Antifoam 204, Antifoam A, Antifoam SE-15, Antifoam SO-25 and Antifoam 289) may be added to the reagent composition according to the present application.

The reagent composition of the application may include ECL labels. The ECL labels may be conventional ECL labels. Examples of electrochemiluminescent groups which may be suitable labels ("ECL labels") for use in the present methods include organometallic compounds where the metal is from, for example, the metals of group VII and VIII. Examples of ECL labels include tris-bipyridyl-ruthenium (RuBpy) and other organometallic compounds where the metal is from, for example, the metals of group VII and VIII, including ruthenium, osmium, rhenium, iridium. These ECL labels are used by a person skilled in the art to label an analyte specific reagent with an electrochemiluminescent group, or to label the analyte itself with an electrochemiluminescent group. The ECL group in a label may comprise an electrochemiluminescent polydendate metal complex, e.g., a polydendate metal complex including heteroaromatic polydentate ligands and a metal chosen from ruthenium, osmium, rhenium, and iridium. For example, the ECL group may comprise a polydendate metal complex, which includes ruthenium and at least one polydentate ligand selected from bipyridyl, substituted bipyridyl, 1,10-phenanthroline and/or substituted 1,10-phenanthroline. Advantageously, the ECL labels are metal chelates. The metal of that chelate is suitably any metal such that the metal chelate will luminesce under the electrochemical conditions which are imposed on the reaction system in question. The metal of such metal chelates may suitably be ruthenium or osmium. The ligands which are linked to the metal in such chelates are usually heterocyclic or organic in nature. The ligands can be polydentate and may be substituted. Suitable polydentate ligands include aromatic heterocyclic ligands, e.g., nitrogen-containing ligands, such as, bipyridyl and phenanthrolyl ligands. For example, the ECL label may include a tris-bipyridyl-ruthenium (Ru(bpy)$_3^{2+}$) moiety.

In one embodiment, the reagent composition of the application contains a labeled analyte and/or a labeled analyte specific reagent, wherein the ECL label is selected from the group consisting of ECL labels disclosed in U.S. Pat. No. 5,310,687 (A) (BPRu=Ru(bpy)2-bpyCO—OSu), U.S. Pat. Appln. Pub. No. 2003/0124572 (A1) (Sulfo-BPRu NHS Ester), European Pat. No. 720614(A1) (Bpy2-Ru-bpy-CO-UEEK-korks.-OSu) and Int. Pat. Appln. Pub. No. WO 2002/027317 (A2) (BPRu-(UE)-25-K and BPRu2-SK4), respectively.

The reagents and mixtures thereof used in the reagent composition might be provided either in liquid, frozen, deep frozen, vaporize frozen, lyophilized, gas, solid or dried form before usage. At least before usage of the reagent composition the reagents are solved in a solvent. The reagent compositions of the present application will be an aqueous solution. In a typical embodiment the reagents are solved in water.

These improved formulations are of particular value in high sensitivity assays. In some embodiments described in the present application, the performance of ECL assays is improved even further through optimal combinations of reagent composition with electrode composition. Such suitable ECL electrode compositions comprise electrodes of Ir, Pt or Carbon.

These advantageous combinations include the aforementioned ECL enhancing carbonic acid amides and suitable preservatives selected from the group consisting of boric acid and/or borate, which both have improved properties. These include a higher dynamic range and an improved ratio of ECL signal from bound label to ECL background signal using the disclosed reagent composition according to the present application. This increased sensitivity is important, for example, in assays that benefit from a lower detection limit (e.g., TroponinT assay (TNThs; Order-No.:05092744), Hepatitis-B envelope antigen assay (HBeAg; Order-No.: 11820583), anti-Thyrotropin receptor assay (anti-TSHR; Order-No.: 04388780)—for details see the example section).

These improved formulations of reagent compositions can give a better precision that may result in a lower detection limit in ECL assays.

Another aspect of the application relates to a reduction of costs due to a reduction of the required volumes of sample, test-specific reagents and/or test reagent. The signal loss for lower reagent volumes can be compensated by using the advantageous reagent composition according to the present application.

Yet another aspect of the application relates to improved systems and apparatus containing the reagent composition of the application and/or improved systems and apparatus adapted to perform the improved methods described herein.

The ECL signal generation can also be improved when the above findings are used either alone or in combination with each other.

Reagent Mixture:

For the determination of ECL the reagent composition according to the present application may be mixed with additional compounds forming a reagent mixture. In an embodiment, the present application provides a reagent mixture for determining ECL, comprising a reagent composition for determining ECL, comprising i) a compound selected from the group of carbonic acid amides of Formula I and Formula II, ii) at least one coreactant, iii) a sample to be investigated and iv) at least one detection reagent labeled with an electrochemiluminescent group.

In an embodiment, the present application provides a reagent mixture for determining ECL, comprising a reagent composition for determining ECL, comprising i) a compound selected from the group of carbonic acid amides of Formula I and Formula II, ii) at least one coreactant, iii) at least one preservative, iv) a sample to be investigated, and v) at least one detection reagent labeled with an electrochemiluminescent group.

In an embodiment, the present application provides a reagent mixture for determining ECL, comprising a reagent composition for determining ECL, comprising i) a compound selected from the group of carbonic acid amides of Formula I and Formula II, ii) at least one coreactant, iii) a preservative selected from the group consisting of boric acid and borate, iv) a sample to be investigated, and v) at least one detection reagent labeled with an electrochemiluminescent group.

In a further embodiment, the present application provides a reagent mixture for determining ECL, comprising a reagent composition for determining ECL, comprising i) a preservative selected from the group consisting of boric acid and borate, ii) at least one coreactant, iii) a sample to be investigated, and iv) at least one detection reagent labeled with an electrochemiluminescent group. In a typical embodiment the reagent mixture comprises the preservative boric acid. In another typical embodiment the reagent mixture comprises the preservative borate.

The present application also provides in an embodiment a reagent mixture for determining ECL, comprising a reagent composition for determining ECL, comprising i) a preservative selected from the group consisting of boric acid and borate, ii) at least one coreactant, iii) a sample to be investigated, iv) a detergent, v) a buffering agent, vi) at least one detection reagent labeled with an electrochemiluminescent group, and vii) comprising a salt and/or an anti-foam agent.

In a further typical embodiment, the present application provides a reagent mixture for determining ECL, comprising a reagent composition for determining ECL, comprising i) a compound selected from the group of carbonic acid amides of Formula I and Formula II, ii) at least one coreactant, iii) a preservative selected from the group consisting of boric acid and borate, iv) a sample to be investigated, v) a detergent, vi) a buffering agent, and vii) at least one detection reagent labeled with an electrochemiluminescent group.

The reagent mixture in addition may comprise at least one detergent and a buffering agent for pH control. Optionally the reagent mixture may comprise a salt and/or an anti-foam agent.

Other test components in the reagent mixture are selected from the group consisting of non-labeled analyte specific reagents, analyte homologs, solid phase coatings and substances that reduce interference.

Use:

An aspect of the present application relates to the use of an improved reagent composition and/or an improved reagent mixture of the present application for performing an electrochemiluminescent detection method.

In an embodiment, the present application provides the use of a carbonic acid amide selected from the group of Formula I and Formula II for performing an electrochemiluminescent detection. In an embodiment, the current application relates to the use of a carbonic acid amide selected from the group of Formula I and Formula II for performing an electrochemiluminescent detection method procedure.

In a typical embodiment, the present application provides the use of carbonic acid amides selected from the group consisting of acetamide, 2-fluoroacetamide, 2-chloroacteamide, propanamide, 2-chloropropanamide, 3-chloropropanamide, butanamide and 2-chlorobutanamide for performing an electrochemiluminescent detection.

In another typical embodiment, the present application provides the use of a carbonic acid amide selected from the group consisting of acetamid, 2-chloroacetamide, propanamide and butanamide for performing an electrochemiluminescent detection. In another embodiment, the present application provides for to the use of a carbonic acid amide selected from the group consisting of acetamid, propanamide and butanamide for performing an electrochemiluminescent detection.

In an embodiment, the present application provides the use of a reagent composition comprising i) a compound selected from the group of carbonic acid amides of Formula I and Formula II, ii) at least one coreactant, and iii) at least one preservative for determination of ECL.

In an embodiment, the present application provides the use of a reagent composition comprising i) a compound selected from the group of carbonic acid amides of Formula I and Formula II, ii) at least one coreactant, and iii) a preservative selected from the group consisting of boric acid and borate for determination of ECL.

In an embodiment the present application provides the use of a reagent composition comprising i) a compound selected from the group of carbonic acid amide selected from the group consisting of acetamide, 2-fluoroacetamide, 2-chloroacteamide, propanamide, 2-chloropropanamide, 3-chloropropanamide, butanamide and 2-chlorobutanamide ii) at least one coreactant, and iii) a preservative for determining ECL.

The reagent composition according to the present application is in an embodiment appropriate for conditioning or regeneration of an ECL measurement cell and for determining an ECL signal. In embodiment said reagent composition is used as a conditioning solution. In an embodiment the reagent composition according to the present application is used for conditioning or regeneration of an ECL measurement cell. In an embodiment said reagent composition comprising a compound selected from the group of carbonic acid amide selected from the group consisting of acetamide, 2-fluoroacetamide, 2-chloroacteamide, propanamide, 2-chloropropanamide, 3-chloropropanamide, butanamide and 2-chlorobutanamide is used for the conditioning or regeneration of ECL measurement cells. In another embodiment said reagent composition comprising a compound selected from the group of carbonic acid amide selected from the group consisting of acetamid, propanamide and butanamide is used for the conditioning or regeneration of ECL measurement cells.

For the use of performing an electrochemiluminescent detection method the reagent composition can be mixed with additional compounds, e.g., a sample to be investigated, at least one detection reagent with an electrochemiluminescent group as well as other components mentioned below supporting the method forming a reagent mixture.

In an embodiment, the present application provides the use of a reagent mixture comprising a reagent composition, a) comprising i) a compound selected from the group of carbonic acid amides of Formula I and Formula II, ii) at least one coreactant, and iii) a preservative, b) a sample to be investigated, and c) at least one detection reagent labeled with an electrochemiluminescent group in the determination of ECL.

The present application provides the use of a reagent mixture comprising a reagent composition for determining ECL, a) comprising i) a compound selected from the group of carbonic acid amides of Formula I and Formula II, ii) at least one coreactant, and iii) a preservative selected from the group consisting of boric acid and borate, b) a sample to be investigated, and c) at least one detection reagent labeled with an electrochemiluminescent group in the determination of ECL.

In a further embodiment, the present application provides for the use of boric acid or borate for performing an electrochemiluminescent detection. Also in an embodiment the present application provides the use of a preservative selected from the group consisting of boric acid and/or borate for performing an electrochemiluminescent detection method procedure.

In an embodiment, the present application provides the use of a reagent mixture comprising a) a reagent composition for determining ECL, comprising i) a preservative selected from the group of boric acid and borate and ii) at least one coreactant, b) a sample to be investigated, and c) at least one detection reagent labeled with an electrochemiluminescent group in the determination of ECL.

In addition the reagent mixture used for determining ECL may comprise components selected from the group consisting of a detergent and a buffering agent for pH control. Optionally the used reagent mixture may comprise a salt and/or an anti-foam agent. Other test components in the reagent mixture are selected from the group consisting of non-labeled analyte specific reagents, analyte homologs, solid phase coatings and substances that reduce interference.

Kits:

One aspect of the application relates to kits comprising, in one or more containers, one or more components of the reagent composition as described herein. These components may be combined, optionally with additional reagents, to form the reagent composition as described herein. The kits may also comprise in an embodiment additional assay related components such as ECL labels, ECL labeled assay reagents, diluents, washing solutions, protein denaturating reagents, enzymes, binding reagents, assay plates, disposables, etc.

In an embodiment, the reagent composition is contained in one or more glass or plastic containers, appropriately labeled with information regarding the reagent composition contents and instructions regarding proper storage and use.

Information regarding the reagent composition contents, lot number, production date, best before date, instructions regarding proper storage and use may be also stored on a RFID chip placed on the glass or plastic containers. The information stored on such RFID chip can be read by an antenna connected to a RFID reader device and further processed in a control means.

In an embodiment some or all of the components of the reagent composition may be stored in an embodiment in a liquid or dry state.

In an embodiment, the present application concerns a kit for measuring ECL, which contains a reagent composition for determining ECL, comprising i) a compound selected from the group of carbonic acid amides of Formula I and Formula II, and ii) at least one coreactant.

In a typical embodiment, the present application provides a kit for measuring ECL, which contains a reagent composition for determining ECL, comprising i) a carbonic acid amide selected from the group consisting of acetamide, 2-fluoroacetamide, 2-chloroacteamide, propanamide, 2-chloropropanamide, 3-chloropropanamide, butanamide and 2-chlorobutanamide, and ii) at least one coreactant.

In another typical embodiment, the present application provides a kit for measuring ECL, which contains a reagent composition for determining ECL, comprising i) a carbonic acid amide selected from the group consisting of acetamide, 2-chloroacteamide, propanamide and butanamide and, ii) at least one coreactant.

In an embodiment, the present application provides a kit for measuring ECL, which contains a reagent composition for determining ECL, comprising i) a compound selected from the group of carbonic acid amides of Formula I and Formula II, ii) at least one coreactant, and iii) a preservative.

In an typical embodiment, the present application provides a kit for measuring ECL, which contains a reagent composition for determining ECL, comprising i) a compound selected from the group of carbonic acid amides of Formula I and Formula II, ii) at least one coreactant, and iii) a preservative selected from the group consisting of boric acid and borate.

In another typical embodiment, the present application provides a kit for measuring ECL, which contains a reagent composition for determining ECL, comprising i) a carbonic acid amide selected from the group consisting of acetamide, 2-fluoroacetamide, 2-chloroacteamide, propanamide, 2-chloropropanamide, 3-chloropropanamide, butanamide and 2-chlorobutanamide, ii) at least one coreactant, and iii) a preservative selected from the group consisting of boric acid and borate.

In another typical embodiment, the present application provides a kit for measuring ECL, which contains a reagent composition for determining ECL, comprising i) a carbonic acid amide selected from the group consisting of acetamide, 2-chloroacteamide, propanamide and butanamide, ii) at least one coreactant, and iii) a preservative selected from the group consisting of boric acid and borate.

In an embodiment, the present application provides a kit for measuring ECL, which contains a reagent composition for determining ECL, comprising at least i) a preservative selected from the group consisting of boric acid and borate, and ii) at least one coreactant.

The aforementioned measures per se already significantly improve the known procedures. Moreover, it is possible to further significantly increase the sensitivity and/or the dynamic measuring range of an analyte detection assay by combining these measures.

The following examples and figures are provided to aid the understanding of methods, reagent composition and kits described herein. It is understood that modifications can be made in the procedures set forth herein without departing from the spirit and scope of the claimed subject matter.

Example 1

ECL Measurements Using Assay Buffers (Reagent Compositions) with Carbonic Acid Amides ECL measurements were carried out using the Roche Elecsys® 2010 device using protocols available for the assays mentioned below.

Various concentrations of compounds selected from the group of carbonic acid amides as indicated in Tables 2, 3 and 4 were added to the following assay buffer:
 180 mM tripropylamine (TPA)
 0.1% polidocanol
 300 mM phosphate buffer
The final pH was adjusted to pH 6.8 using $KOH/H_3PO_4$. The assay buffer was also used as blank value.

The compounds selected form the group of carbonic acid amides (chemical formulas of carbonic acid amides are shown in Table 1) were added to the assay buffer (reagent composition) at the indicated concentrations. Results are reported as signal recovery relative to measurements using an assay buffer lacking these compounds.

Assay buffer background measurements with an assay buffer containing the carbonic acid amides at the concentration shown in Table 2 were performed. Values below 100% indicate a reduced ECL background signal by addition of the selected carbonic acid amide at the indicated concentrations. Reducing the background electrochemiluminescence in the absence of ECL labels is particularly an advantage at low detection levels, where increasing the signal to background ratio (=signal to noise ratio) greatly improves the sensitivity of an assay.

TABLE 2

| | Assay Buffer Background | | | | |
|---|---|---|---|---|---|
| Concentration | 0.25M | 0.1M | 0.01M | 0.001M | 0.0001M |
| 2,2 dichloro-acetamide | 30% | 40% | 70% | 84% | 93% |
| 2-chloroacetamide | 66% | 69% | 80% | 94% | 98% |
| 2-chlorobutanamide | 91% | 79% | 80% | 92% | 98% |
| 2-chlor-N-hydroxy-methylacetamide | 0% | 46% | 97% | 91% | 97% |
| 2-chlor-N,N-dimethyl-acetamide | 64% | 75% | 92% | 99% | 98% |
| 2-chlor-N-methoxy-N-methylacetamide | 0% | 0% | 88% | 99% | 102% |
| 2-chloropropanamide | 70% | 68% | 78% | 93% | 97% |
| 3-chloropropanamide | n.d. | n.d. | 79% | 91% | 96% |
| Acetamide | 79% | 80% | 90% | 95% | 97% |
| Acetoacetamide | n.d. | 55% | 85% | 94% | 98% |
| 2-bromoacetamide | n.d. | n.d. | 39% | 72% | 93% |
| Butanamide | 68% | 68% | 81% | 108% | 108% |
| Formamide | 74% | 75% | 81% | 94% | 98% |
| 2-fluoroacetamide | 73% | 77% | 91% | 101% | 102% |
| 2-hydroxy-acetamide | 93% | 90% | 96% | 100% | 101% |
| Hexanamide | 56% | 53% | 67% | 83% | 90% |
| 2-jodoacetamide | 0% | 0% | 0% | 0% | 34% |
| Propanediamde | 79% | 84% | 92% | 91% | 99% |
| N-methylpropanamide | 88% | 90% | 94% | 98% | 100% |
| 2,2 dimethyl-propanamide | 69% | 68% | 88% | 98% | 99% |
| propanamide (propionamide) | 77% | 74% | 86% | 95% | 88% |
| 2-pyrrolidone | 88% | 84% | 96% | 101% | 100% |

TABLE 2-continued

| | Assay Buffer Background | | | | |
|---|---|---|---|---|---|
| Concentration | 0.25M | 0.1M | 0.01M | 0.001M | 0.0001M |
| 2,5-butanimide | 135% | 103% | 105% | 103% | 98% |
| 2,2,2-triflouro-acetamide | 98% | 85% | 87% | 95% | 99% |
| Pentanamide | 75% | 63% | 73% | 91% | 97% | n.d. = not determined

In an analogous experiment the signals of free label were determined. The free label value represents the signal generated by a solution containing a free ECL label in the absence of microparticles (10 nM RuBpy in the assay buffer). This value is stated in Table 3 relative to the assay buffer without any additional compound in %. This assay format is also known as a homogenous measurement or homogeneous assay format. Values above 100% indicate an enhanced ECL signal by addition of the selected carbonic acid amide at the selected concentration. Results are shown in Table 3.

TABLE 3

| | Free label assay | | | | |
|---|---|---|---|---|---|
| Concentration | 0.25M | 0.1M | 0.01M | 0.001M | 0.0001M |
| 2,2 dichloro-acetamide | 33% | 66% | 145% | 120% | 104% |
| 2-chloroacetamide | 155% | 151% | 131% | 109% | 101% |
| 2-chlorobutanamide | 157% | 147% | 126% | 108% | 100% |
| 2-chlor-N-hydroxy-methylacetamide | 0% | 6% | 103% | 125% | 99% |
| 2-chlor-N,N-dimethylacetamide | 125% | 116% | 103% | 100% | 100% |
| 2-chlor-N-methoxy-N-methylacetamide | 2% | 5% | 124% | 0% | 0% |
| 2-chloro-propanamide | 113% | 155% | 132% | 110% | 102% |
| 3-chloro-propanamide | n.d. | n.d. | 132% | 107% | 100% |
| Acetamide | 141% | 132% | 110% | 102% | 100% |
| acetoacetamide | 6% | 21% | 130% | 104% | 97% |
| 2-bromoacetamide | n.d. | n.d. | 89% | 139% | 110% |
| Butanamide | 145% | 136% | 114% | 103% | 99% |
| Formamide | 134% | 145% | 127% | 111% | 103% |
| 2-fluoroacetamide | 144% | 134% | 111% | 102% | 100% |
| 2-hydroxy-acetamide | 130% | 137% | 109% | 101% | 99% |
| Hexanamide | 118% | 105.7% | 120% | 111% | 103% |
| 2-jodoacetamide | 0% | 0% | 2% | 3% | 127% |
| propanediamde | 123% | 135% | 115% | 115% | 100% |
| N-methyl-propanamide | 106% | 99% | 97% | 98% | 98% |
| 2,2 dimethyl-propanamide | 125% | 120% | 106% | 99% | 97% |
| propanamide (propionamide) | 144% | 135% | 113% | 101% | 99% |
| 2-pyrrolidone | 142% | 130% | 107% | 100% | 99% |
| 2,5-butanimide | 102% | 136% | 107% | 100% | 99% |
| 2,2,2-triflouro-acetamide | 130% | 150% | 116% | 103% | 100% |
| Pentanamide | 151% | 140% | 122% | 108% | 103% | n.d. = not determined

Additionally, the values using the a simplified assay including beads were determined. This artificial assay is an assay including RuBpy labeled microparticles for a high specific signal. This assay format is also known as a heterogeneous measurement or heterogeneous assay format. The difference between the specific artificial assay-signal and the background signal (assay buffer background) using the assay buffer as described above with the additional compounds as indicated as ΔArtificial assay in % relative to assays buffer without any additional compound. Values above 100% indicate an enhanced ECL signal by addition of the selected carbonic acid amide at the selected concentration. Results are shown in Table 4.

TABLE 4

| Concentration | ΔArtificial assay = (artificial assay − assay buffer background) | | | | |
|---|---|---|---|---|---|
| | 0.25M | 0.1M | 0.01M | 0.001M | 0.0001M |
| 2,2 dichloro-acetamide | 73% | 67% | 92% | 122% | 109% |
| 2-chloroacetamide | 160% | 165% | 148% | 113% | 104% |
| 2-chlorobutanamide | 119% | 152% | 149% | 119% | 102% |
| 2-chlor-N-hydroxy-methylacetamide | 100% | 54% | 109% | 121% | 107% |
| 2-chlor-N,N-dimethyl-acetamide | 97% | 115% | 113% | 103% | 104% |
| 2-chlor-N-methoxy-N-methylacetamide | 100% | 100% | 108% | 100% | 95% |
| 2-chloropropanamide | 63% | 109% | 145% | 119% | 104% |
| 3-chloropropanamide | n.d. | n.d. | 148% | 111% | 104% |
| acetamide | 138% | 144% | 123% | 110% | 106% |
| acetoacetamide | n.d. | 61% | 125% | 107% | 98% |
| 2-bromoacetamide | n.d. | n.d. | 68% | 129% | 114% |
| butanamide | 159% | 161% | 131% | 95% | 91% |
| formamide | 51% | 76% | 116% | 110% | 105% |
| 2-fluoroacetamide | 148% | 148% | 118% | 100% | 97% |
| 2-hydroxy-acetamide | 32% | 85% | 108% | 100% | 99% |
| hexanamide | 52% | 59% | 81% | 113% | 109% |
| 2-jodoacetamide | 0% | 0% | 0% | 0% | 125% |
| propanediamde | 50% | 84% | 112% | 108% | 100% |
| N-methylpropanamide | 104% | 106% | 104% | 102% | 100% |
| 2,2 dimethylpropanamide | 147% | 149% | 119% | 103% | 99% |
| propanamide (propionamide) | 157% | 163% | 133% | 111% | 116% |
| 2-pyrrolidone | 117% | 144% | 116% | 100% | 99% |
| 2,5-butanimide | −11% | 84% | 101% | 98% | 103% |
| 2,2,2-triflouro-acetamide | 47% | 130% | 133% | 106% | 100% |
| pentanamide | 129% | 147% | 136% | 119% | 107% | n.d. = not determined

Figure 2:
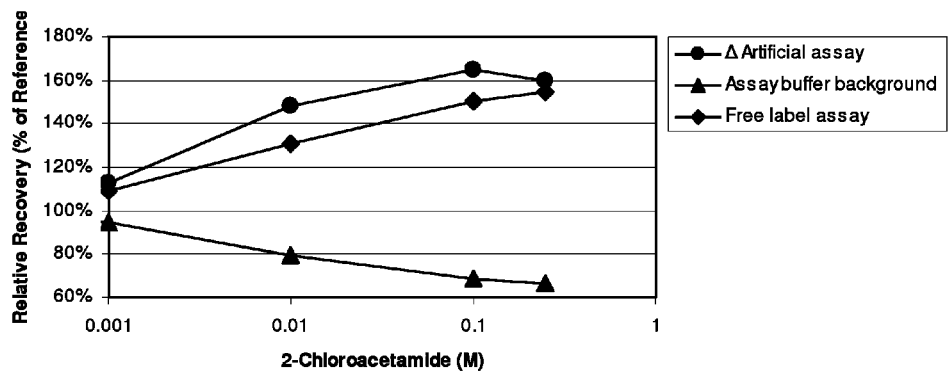
FIG. 2 depicts measurement results with 2-chloroacetamide concentrations of 0.001 M to 1 M (X-axis); relative recovery rate (% of Reference) of the measurement of ΔArtificial assay (artificial assay—assay buffer background), assay buffer background and a free label assay are shown (Y-axis) as discussed in Example 1.
Figure 3:
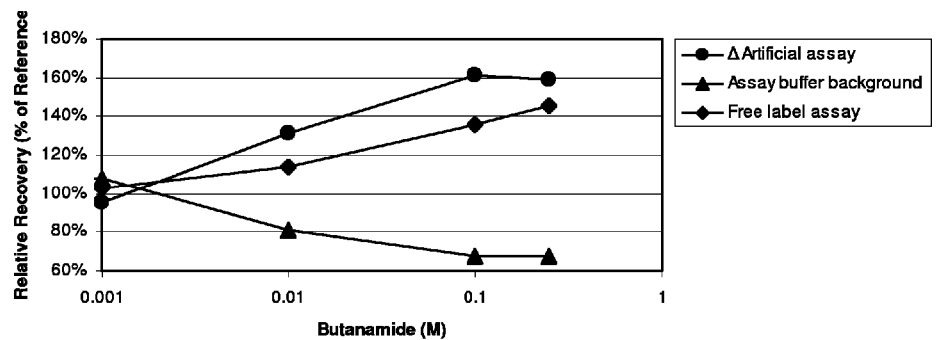
FIG. 3 depicts measurement results with butanamide concentrations of 0.001 M to 1 M (X-axis); relative recovery rate (% of Reference) of the measurement of ΔArtificial assay (artificial assay—assay buffer background), assay buffer background and free label assay are shown (Y-axis) as discussed in Example 1.
Figure 4:
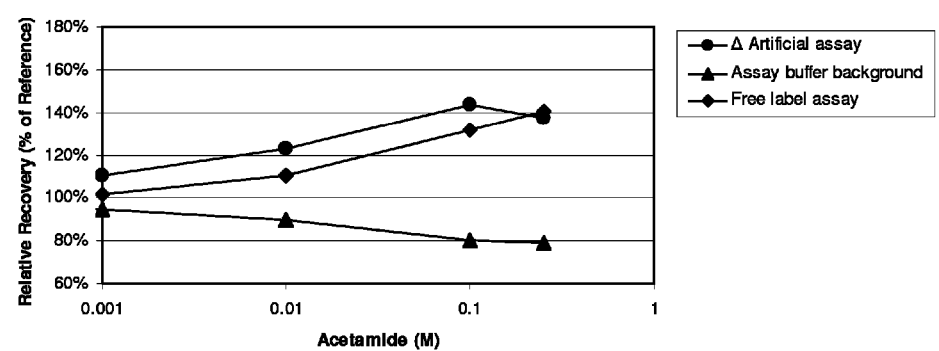
FIG. 4 depicts measurement results with acetamide concentrations of 0.001 M to 1 M (X-axis); relative recovery rate (% of Reference) of the measurement of ΔArtificial assay (artificial assay—assay buffer background), assay buffer background and free label assay are shown (Y-axis) as discussed in Example 1.

In FIG. 1, a graph containing results for propanamide as shown in Tables 2, 3 and 4 is presented. In FIG. 2 a graph containing results for 2-chloroacetamide as shown in Tables 2, 3 and 4 is presented. In FIG. 3 a graph containing results for butanamide as shown in Tables 2, 3 and 4 is presented. In FIG. 4 a graph containing results for acetamide as shown in Tables 2, 3 and 4 is presented.

Example 2

Boric Acid as a Signal Enhancing Preservative

ECL measurements were carried out using the Roche Elecsys® 2010 device using the recommended protocols for the assays mentioned below.

The following ECL assay buffer was used to determine the blank value:
   180 mM tripropylamine (TPA)
   0.1% polidocanol
   0.1% Oxaban A
   300 mM phosphate buffer
To this assay buffer increasing amounts of boric acid were added as indicated. The final pH was adjusted to pH 6.8 using KOH/H$_3$PO$_4$.

Assay buffer background measurements with an assay buffer containing boric acid at the concentrations shown in Table 5 were performed. The free label value represents the signal generated by a solution containing a free ECL label in the absence of microparticles (10 nM RuBpy in the assay buffer, homogenous measurement) relative to the assay buffer without any additional compound in %. The artificial assay is an assay including RuBpy labeled microparticles for a high specific signal. As a commercial in vitro diagnostic assay, the Elecsys® TSH assay (Thyrotropin assay for Elecsys®; Order-No.: 11731459) was used to determine ΔTSH. The TSH calibrator 1 (TSH Cal set; Order-No.: 04738551) as a low level calibrator (no analyte present) was used in the TSH assay giving a background signal (TSH Cal 1); the TSH calibrator 2 was used in the TSH assay to give a high signal value (TSH Cal 2).

Figure 5:
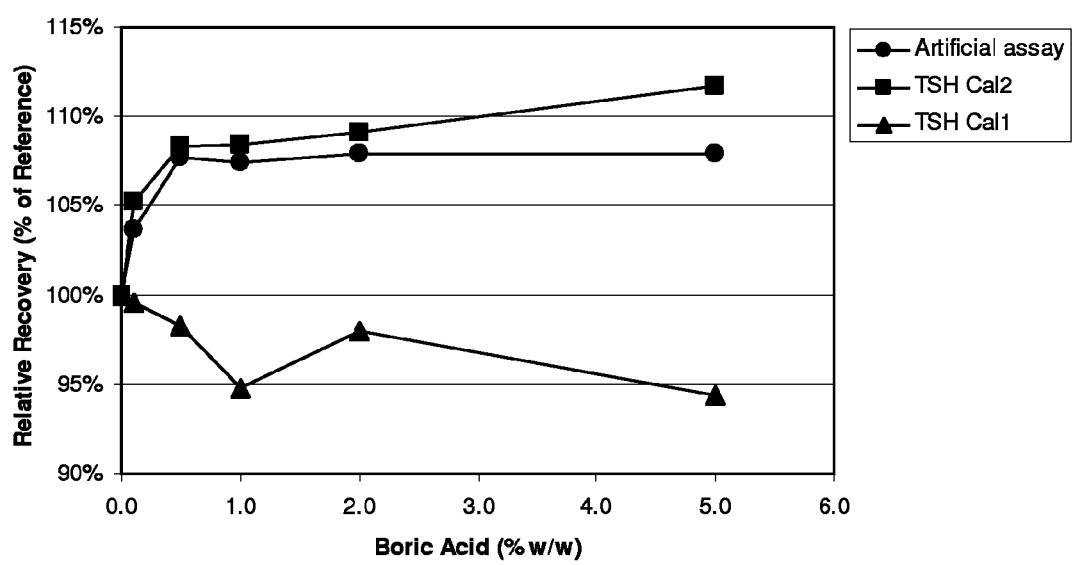
FIG. 5 depicts measurement results with boric acid concentrations of 0 to 5% (X-axis); the artificial assay was used as an example for a high specific signal; the TSH calibrator 1 as a low level calibrator gives a background signal (TSH Cal 1); the TSH calibrator 2 gives a signal at a high detection level (TSH Cal 2). The results are plotted as % of the reference reagent composition without addition of boric acid as discussed in Example 2.

The results for the artificial assay, TSH Cal1 and TSH Cal 2 are plotted in FIG. 5 as the relative recovery in % of the reference assay buffer without addition of boric acid. In particular, the following measurements were performed:

TABLE 5

| Relative recovery (% of Reference) - Comparison to an assay buffer without boric acid | | | | | | |
|---|---|---|---|---|---|---|
| Boric acid conc. | 0% | 0.1% | 0.5% | 1.0% | 2.0% | 5.0% |
| Assay buffer background | 100% | 103% | 102% | 98% | 103% | 103% |
| Free label assay | 100% | 100% | 99% | 97% | 93% | 93% |
| Artificial assay | 100% | 104% | 108% | 107% | 108% | 108% |
| TSH Cal2 | 100% | 105% | 108% | 108% | 109% | 112% |
| TSH Cal1 | 100% | 100% | 98% | 95% | 98% | 94% |

Addition of boric acid as a preservative in an assay buffer improves the specific heterogeneous signal, especially in the artificial assay and in the determination of TSH Cal2.

Example 3

Effect of Assay Buffers Containing Propanamide and Boric Acid on the Lower Detection Limit of Elecsys® Assays The lower detection limit with several commercial in vitro diagnostic assays (HBeAg: Roche Order-No.: 11820583, Anti-TSHR: Roche Order-No.: 04388780, TNThs: Roche Order-No.: 05092744) was determined to compare two assay buffer preparations.

Assay buffer A:
   180 mM TPA, 0.1% polidocanol, 300 mM phosphate buffer, 0.1% Oxaban A
Assay buffer B:
   180 mM TPA, 0.1% polidocanol, 50 mM propanamide, 300 mM phosphate buffer, 1% boric acid
The final pH of both assay buffers A and B was adjusted to pH 6.8 using KOH/H$_3$PO$_4$.

The three commercially available assays mentioned above have been analyzed to show the effect of the carbonic acid amide propanamide and the preservative boric acid on the assay performance detecting very low analyte concentrations.

The assays were measured on a Roche Elecsys® analyzer and calibrated as described in their package inserts. To calculate the lower detection limit the signals of a sample without analyte (HBeAg, anti-TSHR) or with a very low analyte concentration (TNThs) were determined. The standard deviation of the 21-fold determination was calculated, multiplied by 2 (2SD) or 3 (3SD) and added (HBeAg, TNThs), or subtracted (antiTSHR, competitive assay) to the mean of the signal. The corresponding concentration of the calculated signals was then determined using the calibration curve for each assay. For samples with a low analyte concentration (TNThs) the analyte concentration of the sample was subtracted from these calculated concentrations.

The three assays benefit from the improved reagent composition containing a carbonic acid amide according to the present application as well as containing boric acid, which has also a preservative function. The results for HBeAg, anti-TSHR and TNThs assays are shown in Tables 6, 7, and 8, respectively.

TABLE 6

| HBeAg | Lower detection limit [u/ml] | |
|---|---|---|
| | 2 SD | 3 SD |
| Assay buffer A | 0.0030 | 0.0044 |
| Assay buffer B | 0.0018 | 0.0030 |

TABLE 7

| anti-TSHR | Lower detection limit [u/ml] | |
|---|---|---|
| | 2 SD | 3 SD |
| Assay buffer A | 0.324 | 0.500 |
| Assay buffer B | 0.218 | 0.332 |

TABLE 8

| TNThs | Lower detection limit [pg/ml] | |
|---|---|---|
| | (2SD) - Conc. of sample | (3SD) - Conc. of sample |
| Assay buffer A | 1.193 | 1.832 |
| Assay buffer B | 0.782 | 1.140 |

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or the representation. These terms are also utilized herein to represent the degree by which a quantitative representation may vary from a stated reference without resulting in a change in the basic function of the subject matter at issue.

What is claimed is:

1. A method for detecting an analyte in a sample, comprising the steps of:
   a) incubating the sample with a detection reagent labeled with an electrochemiluminescent group to provide an analyte-bound labeled detection reagent;
   b) electrochemically triggering the release of electrochemiluminescence by the analyte-bound labeled detection reagent, which is incubated with a reagent composition for determining electrochemiluminescence (ECL), comprising:
      i) at least one electrochemiluminescence (ECL) coreactant, which is selected from the group consisting of tertiary amines, oxalate and persulfate;
      ii) a concentration of 0.01 M to 0.25 M of at least one carbonic acid amide selected from 2-pyrrolidone and compounds having a formula:

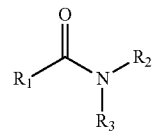

Formula I wherein $R_1$ is H, or a $C_1$-$C_5$ alkyl group, optionally substituted with a single chlorine or fluorine atom, $R_2$=H, and $R_3$=H; and
   c) determining the electrochemiluminescence (ECL) signal thereby detecting the analyte.

2. The method according to claim 1, wherein the measurement of the analyte in the sample using ECL is performed in an aqueous solution.

3. The method according to claim 1, wherein the at least one carbonic acid amide comprises acetamide, 2-fluoroacetamide, 2-chloroacteamide, propanamide, 2-chloropropanamide, 3-chloropropanamide, butanamide, 2-chlorobutanamide or a mixture thereof.

4. The method according to claim 1, wherein the reagent composition further comprises a preservative.

5. The method according to claim 4, wherein the reagent composition comprises 0.1% to 5% of the preservative.

6. The method according to claim 4, wherein the preservative comprises boric acid, borate or a mixture thereof.

7. The method according to claim 1, wherein the at least one ECL coreactant comprises a compound selected from the group consisting of tertiary amines, oxalate and persulfate.

8. A method for detecting an analyte in a sample, comprising the steps of:
   a) incubating the sample with a detection reagent labeled with an electrochemiluminescent group to provide an analyte-bound labeled detection reagent,
   b) electrochemically triggering the release of electrochemiluminescence by the analyte-bound labeled detection reagent, which is incubated with a reagent composition comprising:
      i) at least one electrochemiluminescence (ECL) coreactant, which is selected from the group consisting of tertiary amines, oxalate and persulfate,
      ii) a concentration of 0.01 M to 0.25 M of at least one carbonic acid amide selected from 2-pyrrolidone and compounds having a formula

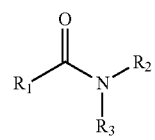

Formula I wherein $R_1$ is —H, or a $C_1$-$C_5$ alkyl group, optionally substituted with a single chlorine or fluorine atom, $R_2$=H, and $R_3$=H; and
   c) determining the electrochemiluminescence (ECL) signal thereby detecting the analyte.

9. The method of claim 8, wherein $R_1$ is a $C_1$-$C_5$ alkyl group.

10. The method of claim 8, wherein $R_1$ is a monochloro-substituted $C_1$-$C_5$ alkyl group.

11. The method of claim 8, wherein the at least one carbonic acid amide comprises acetamide, 2-fluoroacetamide, 2-chloroacteamide, propanamide, 2-chloropropanamide, 3-chloropropanamide, butanamide, 2-chlorobutanamide or a mixture thereof.

12. The method of claim 8, wherein the reagent composition further comprises boric acid, borate or a mixture thereof.

13. The method of claim 12, wherein the reagent composition further comprises a detergent selected from the group consisting of fatty acid alcohol ethoxylates, alkylpolyglucosides, octylglucosides and mixtures thereof.

14. The method of claim 8, wherein the reagent composition further comprises (a) boric acid, borate or a mixture thereof, (b) polidocanol and (c) or 4,4-dimethyl oxazolidine; and the ECL coreactant comprises tripropylamine.

15. The method of claim 8, wherein the reagent composition comprises the at least one carbonic acid amide in a concentration of 0.01 M to 0.25 M;

the at least one carbonic acid amide comprises acetamide, 2-chloroacetamide, propanamide and butanamide; the ECL coreactant comprises tripropylamine; and the reagent composition further comprises 0.1 to 5% boric acid, borate or a mixture thereof.

16. The method of claim 8, wherein the labeled detection reagent is immobilized on a solid phase.

\* \* \* \* \*